United States Patent [19]

Fuller

[11] Patent Number: 4,900,514
[45] Date of Patent: Feb. 13, 1990

[54] BREATH ANALYZER MOUTHPIECE SYSTEM

[75] Inventor: Kip L. Fuller, Denver, Colo.

[73] Assignee: Guardian Technologies, Inc., Cincinnati, Ohio

[21] Appl. No.: 45,827

[22] Filed: May 1, 1987

[51] Int. Cl.[4] .............................................. G01N 1/00
[52] U.S. Cl. ...................................... 422/84; 55/465;
73/27 R; 128/639; 128/719; 128/730; 285/328;
285/376; 285/396; 285/402
[58] Field of Search .................... 73/23, 27 R;
128/719–730, 639; 55/465; 285/376, 402, 329,
396, 328; 422/84, 85; 436/132, 900

[56] References Cited

U.S. PATENT DOCUMENTS

| | | |
|---|---|---|
| 718,157 | 1/1903 | Riber .................................. 285/329 |
| 1,386,210 | 8/1921 | Thomas ............................... 285/376 |
| 3,187,745 | 6/1965 | Baum et al. ......................... 128/639 |
| 3,433,231 | 3/1969 | Siragusa ........................... 55/465 X |
| 3,474,775 | 10/1969 | Johnson ............................. 128/639 |
| 3,809,067 | 5/1974 | Hoppesch ........................... 128/719 |
| 3,858,573 | 1/1975 | Ryan et al. ......................... 128/730 |
| 3,880,591 | 4/1975 | Burroughs ............................ 23/259 |
| 4,292,978 | 10/1981 | Guth ............................... 128/719 X |
| 4,564,021 | 1/1986 | Siegmann et al. . |

FOREIGN PATENT DOCUMENTS 2054153 2/1981 United Kingdom .

Primary Examiner—Barry S. Richman
Assistant Examiner—Timothy M. McMahon
Attorney, Agent, or Firm—Wood, Herron & Evans

[57] ABSTRACT

A mouthpiece system for deterring evasion of an alcohol breath test particularly a test wherein a breath sample is delivered without human supervision. The system includes a mouthpiece configured so as to render difficult the delivery of artificial breath samples through the use of hoses, balloons and the like. The mouthpiece has an oversize upper surface which includes a tapered lip around the mouthpiece inlet to receive the mouth of the user. The lip is surrounded by a wide apertured ring which, together with the lip, will not readily form an effective connection with a balloon or hose. An electrode on the mouthpiece is used for sensing and/or signalling the user. The impedance in contact with the electrode is sensed during testing to insure it falls within a range expected for a human user to deter use of evasion using filters or bogus gas delivery devices. Continuity of the impedance during testing is monitored to detect attempts to pass the mouthpiece to an accomplice. The electrodes are also connectable to a signal generator to cue the user to take a predetermined action at an appropriate time. The sensing and signalling functions may be time multiplexed or superposed to permit use of a single electrode to perform both functions.

17 Claims, 4 Drawing Sheets

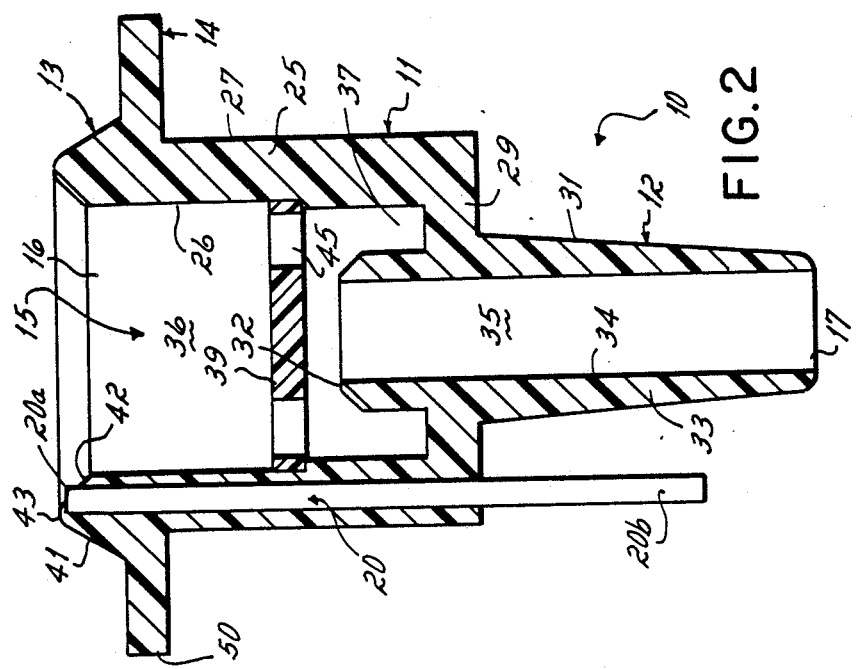
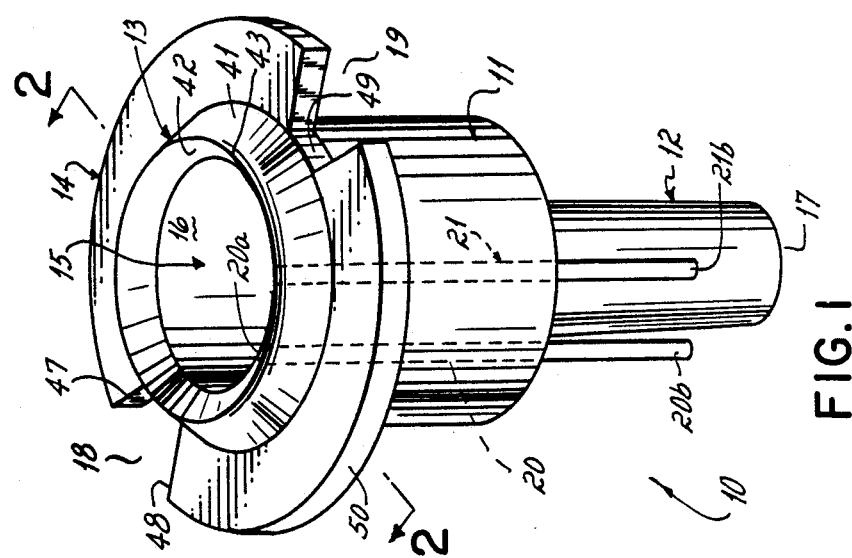

BREATH ANALYZER MOUTHPIECE SYSTEM

The present invention relates to breath analyzers and more particularly to mouthpieces for breath analyzers adapted for use without supervision to test for user alcohol consumption.

BACKGROUND OF THE INVENTION

Breath analyzers such as the portable breath testers used by police for the screening of drivers suspected of driving while under the influence of alcohol require the delivery of a sustained breath sample by the person being tested. Delivery of a proper sample requires the tested person or user to breathe into a sampling head connected to the tester. The sampling head is fitted with a mouthpiece against which the mouth of the user is placed. Such testers are described for example in U.S. Pat. No. 3,764,270 issued to Collier et al. Because the use of conventional breath testers usually occurs under the supervision of a police officer or is voluntary, there is little danger that the sample of gas which is tested will be other than an authentic sample of the breath of the specified person. There are other applications of portable breath analyzers, however, where the authenticity of the breath sample cannot be so easily assured.

For example, sometimes a breath alcohol test is performed by a test subject without human supervision. Where the test subject fears failing the test, he or she may resort to various techniques aimed at circumventing the test including attempts to provide a false sample to the test apparatus. An example of an application in which this is a problem is the breath analyzer incorporated into an ignition interlock system of an automobile or other equipment. Such a system is described in U.S. Pat. No. 4,093,945 issued to Collier et al expressly incorporated herein by reference in its entirety. Vehicle interlock systems, as they are commonly referred to, link an alcohol breath tester to the ignition system of a vehicle such as an automobile. They operate by requiring the user to pass a breath alcohol test before the user's vehicle can be started. Only the delivery of a breath sample with an alcohol content below a predetermined threshold level will enable the ignition system to start the user's engine. Conscientious drivers may install vehicle interlocks in their automobiles as a safety measure and use them voluntarily. On the other hand, the use of an interlock is frequently compelled to some degree. For example, a teen who borrows a family vehicle equipped with an interlock may not be a truly voluntary user. Moreover, the installation of a vehicle interlock is increasingly dictated by court order as a condition for allowing persons convicted of driving under the influence of alcohol to continue to drive.

Another case where breath testing may be performed without direct supervision and where attempts at evasion may be a problem is in a "home arrest" or remote confinement system wherein a prisoner is confined to a designated location and monitored from another location for compliance with behavioral restrictions including abstinence from substances such as alcohol. Such a system is disclosed in co-pending, commonly assigned U.S. patent application Ser. No. 07/041,698 entitled "Remote Confinement System" which is expressly incorporated herein by reference in its entirety.

In the use of a vehicle interlock system, or a remote confinement system which monitors a detainees' abstinence from alcohol, there is usually no supervision by a police officer or other person of the performance of the breath test by the person using the device. Thus, the opportunity exists for the user to attempt to circumvent the test by providing a bogus sample to the tester in lieu of an actual breath sample. Artificial samples may be attempted to be delivered by balloons or hoses attached to the mouth of the tester. If successful, the test apparatus may erroneously analyze this gas as it would an authentic breath sample and enable the starting of the engine. Subjects may also attempt to circumvent the interlock by passing the breath sampling mouthpiece to an accomplice who has not been drinking in excess. The accomplice cooperates with the intended subject by providing a substitute breath sample.

A vehicle interlock system which is specially adapted to permit unsupervised confirmation of the identity of a designated user is described in detail in co-pending U.S. patent application Ser. No. 907,881 which is expressly incorporated herein by reference in its entirety. In that system, the designated test subject is trained to perform an identity-confirming act which is not readily learnable in fewer than a certain number of attempts. Successful performance of this act within a predetermined number of attempts confirms the identity of the subject and permits the breath test to be passed if the breath is below a specified alcohol limit. The system requires that at least a portion of the identity-confirming act, which preferably consists of a coded sequence of timed breath pulses and pauses, to take place substantially contemporaneously with at least a portion of the delivery of the breath sample to be measured. This helps to avoid circumvention by having the designated subject perform the identity-confirming act but having an accomplice who has not been drinking in excess deliver a substitute breath sample.

One may also attempt to defeat alcohol breath tests, particularly those required by vehicle interlock systems, through the use of filters, such as charcoal filters, which tend to remove alcohol from the breath sample being delivered. Such attempts are made by placing a filter over the mouthpiece of the breath tester and then blowing through the filter into the mouthpiece. Some filters can remove enough alcohol from the breath sample entering the sampling tube to permit the breath test to be evaded by a prospective driver whose unfiltered breath exceeds the permissible alcohol limit.

Accordingly, there is a need for an improved mouthpiece for use with alcohol breath testers, particularly those used without supervision, to reduce the likelihood of the success of the abuses discussed above. As such, it is an objective of the present invention to provide a mouthpiece for a breath tester which will effectively deter efforts directed to circumventing the delivery of a valid breath sample, even when the test is performed without supervision.

It is a further objective of the present invention to provide a mouthpiece to which methods of delivering an artificial sample are difficult to adapt.

It is a further objective of the present invention to provide a mouthpiece for a breath analyzer which may be adapted to help detect, and therefor deter, attempts to transfer the mouthpiece between the desired test subject and an accomplice or a bogus delivery device such as a balloon or gas bottle.

It is yet a further objective of the present invention to provide a mouthpiece for a breath analyzer which effectively deters the use of filtering devices to reduce the alcohol content of the breath.

It is a still further objective of the present invention to provide a mouthpiece adapted to cue the test subject to begin or cease some phase of the test sequence such as the performance of the identity-confirming act or delivery of a breath sample.

It is a further objective of the present invention to provide such a mouthpiece wherein cuing is accomplished by direct electrical stimulation to further frustrate attempts to deliver a bogus sample by filter means or the like and to make teaching of the identity-confirming act to an accomplice more difficult.

SUMMARY OF THE INVENTION

According to the present invention, a mouthpiece for a breath analyzer is provided which will allow the formation of a substantially airtight seal between the mouthpiece inlet and the lips and mouth of a user, but which will not easily allow the formation of an effective connection between the mouthpiece and a hose, balloon, or similar device capable of delivering air or other substantially alcohol-free gas. More particularly, the present invention provides a mouthpiece with a shallow lip surrounding the breath inlet. The lip is tapered in opposing directions so that a balloon or hose cannot be readily held in place thereon. In addition, the present invention provides that the surface of the mouthpiece surrounding the inlet is bounded with a wide ring. The ring enlarges the upwardly facing surface of the mouthpiece to help prevent its encirclement by an ordinary hose, balloon or the like. In accordance with certain other principles of the present invention, the ring is provided with voids such as apertures or deep notches along its edge to deter attempts to form an effective connection with the mouthpiece inlet by surrounding the ring with the neck of a balloon, large hose or other conduit. To further deter connection of mouthpiece 10 to a hose or bogus gas delivery devise, ring 14 may be formed in some shape other than circular such as elliptical or other arbitrary shape.

According further to the present invention, a mouthpiece is provided having a pair of electrically conductive electrode elements connectable to circuitry associated with the interlock to perform at least one of a number of functions. By detecting any interruption in the electrical continuity between two electrodes on the surface of the mouthpiece rim caused by a removal of the user's mouth from the device during a test sequence, attempts to transfer the mouthpiece between the test subject and an accomplice or bogus gas delivery device can be detected. Further, the electrical impedance across the elements can be monitored to determine whether they fall within an expected range for a human user. This deters connection to artificial devices which are more conductive or less conductive than a typical human's mouth or lips.

Furthermore, the present invention contemplates the use of the electrode elements as electrical signalling means on the surface of the mouthpiece for delivering an electrical cue signal in the form of a perceptible electrical pulse to signal the user to begin or stop the delivery of the breath sample or to perform an identity-confirming act. The electrode elements are positioned to make contact with the users' mouth or lips when the mouthpiece is used properly so that placement of a filter between the mouthpiece and the users' mouth or lips will prevent the receipt of the signal by the user and will render unlikely the proper timing of the test sequence. In addition, failure by the subject to maintain continuous mouth contact with the mouthpiece will greatly increase the likelihood that receipt of the signal will be missed and a failure of the test will occur.

These and other objects and advantages of the present invention will be more readily apparent from the following detailed description of the drawings in which:

BRIEF DESCRIPTION OF THE DRAWINGS

FIG. 1 is an isometric drawing of a breath analyzer mouthpiece according to the principles of the present invention.

FIG. 2 is a cross-sectional elevational view of the mouthpiece along line 2—2 of FIG. 1.

DETAILED DESCRIPTION OF THE INVENTION

Figure 5:
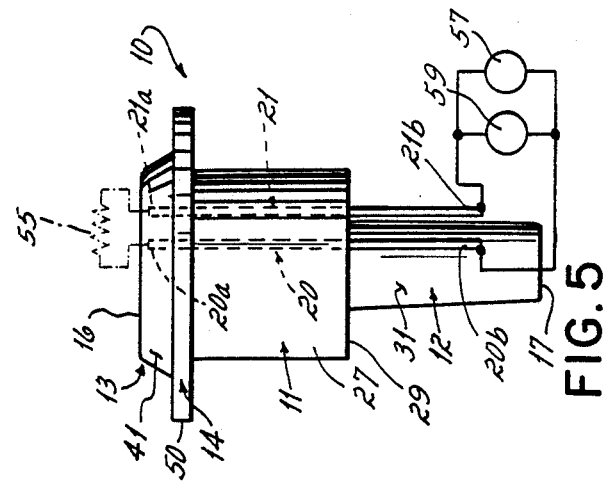
FIG. 5 is an elevational view of the mouthpiece with a schematic block diagram showing circuitry which cooperates with the mouthpiece electrodes.

Referring initially to FIG. 1, a mouthpiece 10 according to principles of the present invention is illustrated. The mouthpiece 10 includes a molded plastic body 11 which is generally cylindrical in shape, an inwardly tapering mounting base 12 of circular cross-section formed integrally of the body 11 and extending downwardly from the base thereof, a tapered annular lip 13 surrounding the body 11 at the upper edge thereof and a notched planar ring 14 extending outwardly from the base of lip 13. The lip 13 and the ring 14 are also integrally formed of the plastic body 11 along with the base 12. In the embodiment illustrated, ring 14 is generally circular. However to further frustrate attempts to couple mouthpiece 10 to a hose or similar conduit which is likely to be circular, ring 14 may take the form of an ellipse or other arbitrary irregular shape.

The body 11, the base 12, the lip 13 and the ring 14 are generally circular in cross-section and share a common axis. An air-tight passage 15 extends through the mouthpiece 10 coaxially with the body 11, base 12, lip 13 and ring 14. The passage 15 has an inlet 16 at the lip 13 and an outlet 17 at the lower end of the base 12. The lip 13 is configured to permit a substantially air tight seal with the mouth of a user so that a breath sample can be delivered into the inlet 16 of the passage 15. The base 12 is configured to connect to a mating fitting on the sampling head of a breath tester or vehicle interlock (not shown) and to thereby form a continuous air passage from the mouth of the user at the inlet 16 of the passage 15 to the sampling head of the breath tester at the outlet 17 of the mouthpiece 10.

The ring 14 is provided with apertures or void areas intended to frustrate attempts to make an effective connection between ring 14 and a bogus gas delivery device. The form of the apertures is entirely arbitrary and may comprise a single aperture or plural apertures. However, the total aperture area should be large to provide a low resistance flow path. About 0.5 square inches of total opening area or more is desirable. In the embodiment shown, the apertures are in the form of a pair of diametrically opposed notches 18 and 19. Voids such as notches 18 and 19 which widen toward their open side at the periphery of ring 14 or other shapes not closed on all sides are preferable since they are not readily plugged with chewing gum or the like.

A pair of conductive electrode elements 20 and 21 in the form of pins of stainless steel or other non-corrosive material extend parallel to the axis of the mouthpiece 10 and are imbedded in the wall of the body 11. Electrode elements 20, 21 may be insert molded or pressed into mating holes after body 11 is formed. The upper ends 20a and 21a of electrode elements 20 and 21 extend through the upper surface of the lip 13 at the top of the mouthpiece 10 near the inlet 16. Prong portions 20b and 21b of electrode elements 20 and 21, respectively, extend downwardly from body 11 adjacent the exterior surface of the base 12. The configuration of the components of the mouthpiece 10 can be better understood with reference to the cross-sectional drawing of FIG. 2.

Referring now to FIG. 2, the mouthpiece 10 is shown with the body 11, the base 12, the lip 13, and the ring 14 formed of a single piece of electrically non-conductive molded plastic material such as polycarbonate or acronitrile butadiene styrene (A.B.S.). In the embodiment shown, body 11 is generally cylindrical having a wall 25 of generally uniform thickness bounded by an inner cylindrical surface 26 and an exterior cylindrical surface 27. However, except as otherwise indicated, body 11 may be in the form of any desired shape. At its lower end, body 11 has an annular floor 29 which forms a closed surface extending from the inside surface 26 of the wall 25 of body 11 to a tapered exterior surface 31 of the base 12. The base 12 has an upper end 32 which projects inwardly ⅛ to ¼ inch above the floor 29 of the body 11. The base 12 extends downwardly to its lower end which forms the outlet 17 of the interior passage 15 of the mouthpiece 10. The base 12 is defined at its sides by the walls 33 of circular horizontal cross-section which are bounded by their exterior surface 31. The surface 31 is a downwardly tapered surface extending from the floor 29 of the body 11 to the outlet 17 of the mouthpiece 10. The base 12 has an interior cylindrical surface 34. This geometry of the mouthpiece 10 divides the inner passage 15 of the mouthpiece 10 into a lower chamber 35 within base 12 and an upper chamber 36 within the body 11. It should be noted that while various structural elements including body 11, base 12 and ring 14 have been described as circular in cross section which provides a pleasing aesthetic appearance, such shapes are not essential for proper operation of mouthpiece 12 and that in light of the present disclosure, those skilled in the art will recognize that other shapes may be adopted.

The inwardly projecting upper end 32 of the base 12 above floor 29, together with the wall 25 of body 11, defines an annular trap 37 which surrounds the raised upper end 32 of the base 12 to inhibit saliva, breath condensation formed in the upper chamber 36 of the passage 15 or foreign matter from proceeding down through the lower passage 35 to the interior of the breath tester to which it is connected. Within the upper chamber 35 is a baffle 39 in the form of an apertured plastic disk which is press or snap fitted inside the chamber 36 spanning the distance across the inner surface 26 of the wall 25 of the body 11.

The lip 13 defines the upper edge of the walls 25 of the body 11. The upper surface of the lip 13 is an inverted V-shape having an outwardly tapered surface 41 tapered at about 30° to the vertical, and an inwardly tapered surface 42, tapered at about 45° to the vertical. A radiused or slightly flattened upper ridge 43 defines the uppermost edge of the mouthpiece 10 and the boundary of the inlet 16 to the passage 15 of the mouthpiece 10. Upper ridge 43 extends between and connects tapered surfaces 41 and 42. The inlet 16 is, in the illustrated embodiment, approximately 0.426 inches in diameter.

Figure 3:
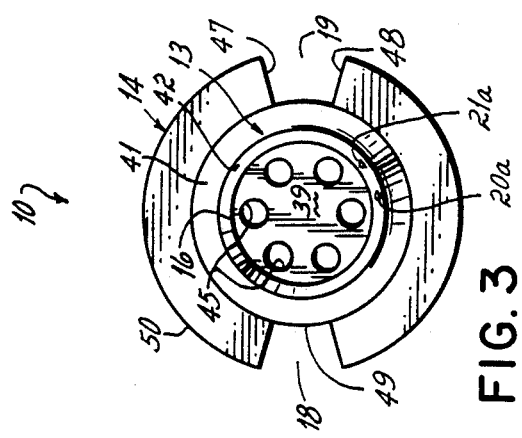
FIG. 3 is a top view of the mouthpiece shown in FIGS. 1–2.

Referring now to FIG. 3, the upper extremes of the mouthpiece 10 and the configuration of baffle 39 can be better appreciated. The lip 13 with its upwardly facing, outwardly tapered surface 41, inwardly tapered surface 42 and upper ridge 43 are there shown encircling the inlet 16 to the passage 15. As seen through the inlet 16, the passage 15 is spanned by the baffle 39 which, in the illustrated embodiment includes six equally spaced apertures or holes 45 disposed in a circular pattern about the axis of the mouthpiece 10 near the periphery of disc 39. The circle which defines the pattern of the holes 45 is of greater diameter than the passage 35 of the base 12 and the holes 45 are themselves sufficiently small in diameter so that no direct linear path is presented from the inlet 16 to the outlet 17. By blocking a direct linear path between the central portion of inlet 16 and the mouth of mounting base 12, baffle 39 helps prevent foreign substances and saliva from entering the breath tester to which the mouthpiece 10 is attached. It should be noted that the choice of the shape, number and arrangement of holes 45 is arbitrary so long as their total area is large enough as to not unduly restrict the flow of breath and so long as the portion of baffle 39 disposed directly above the mouth of base 12 is substantially solid to block the direct flow of foreign matter from inlet 16 into lower passage 35.

The ring 14 can also be seen more clearly in FIG. 3 as having therein a pair of diametrically opposed notches 18 and 19. These notches are each bounded on their closed sides by a pair of tapered surfaces 47 and 48 and by the outer edge 49 of the lip 13 which defines the boundary between the outwardly tapered surface 41 of the lip 13 and the upper surface of the ring 14. Notches 18 and 19 are each open at their outermost extent between the points where tapered surfaces 47 and 48 meet the outer edge 50 of ring 14. The outermost edge 50 of the disk 14 comprises a broken circle approximately one inch in diameter.

Figure 4:
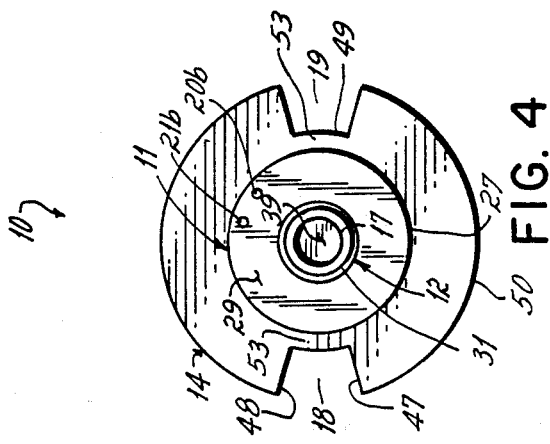
FIG. 4 is a bottom view of the mouthpiece as shown in FIGS. 1–3.

In the bottom view of the mouthpiece 10 of FIG. 4, the notches 18 and 19 of the ring 14 are better illustrated with surfaces 47 and 48 shown extending from the outer edge 50 of the ring 14 to the inner edge 49 which defines the inner radius of the notches 18 and 19. The inner edge 49 is at a radius greater than the outer surface 27 of the body 11 and thus is spaced therefrom by the width of a ring segment 53.

Also in FIG. 4, the taper of base 12 can be seen as downward exposure of its outer surface 31. The outlet 17 of the mouthpiece 10 is defined by the extreme lower edges of the base 12 bounded by the inner and outer surfaces 34 and 31, respectively. The tapered outer surface 31 joins the floor 29 of the body 11 at one end and the edges at the lower end of the base 12 at the other ends.

In FIGS. 3 and 4, the spacing of the conductive electrode elements 20 and 21 is illustrated. The upper extent 20a, 21a of electrode elements 20 and 21, illustrated in FIG. 3, are almost flush with, but preferably protrude slightly from, the tapered surface 42 of the lip 13. Electrode elements 20, 21 function as electrodes which will form electrical contacts between the lips of the user and the circuitry of the vehicle interlock or breath tester. When mouthpiece 10 is in use, the lips of the test subject will form an impedance shunting the two ends of the electrode elements 20 and 21 to form a closed circuit through components provided in the breath tester as illustrated in block diagram form in FIG. 5.

Figure 6:
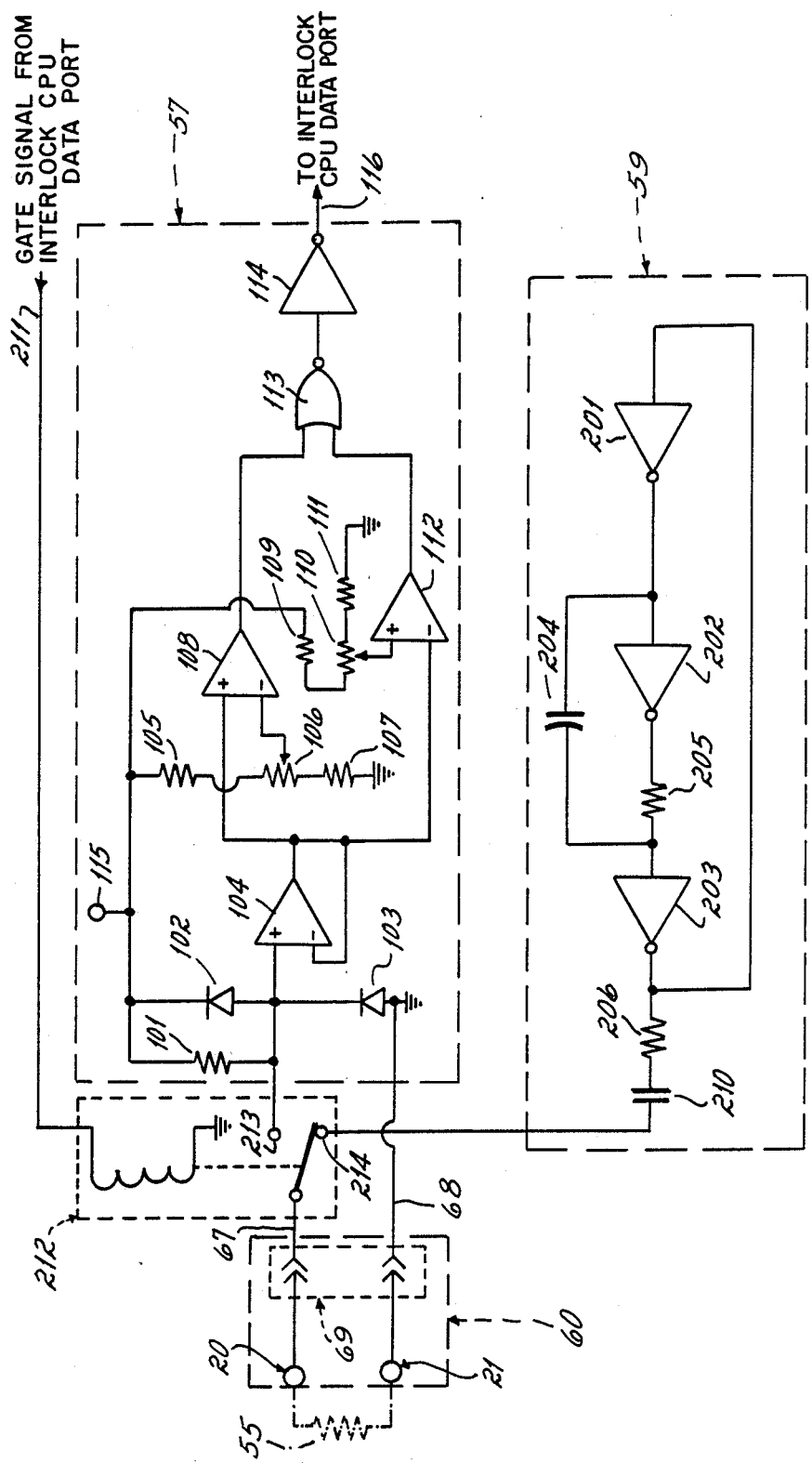
FIG. 6 is a schematic diagram further illustrating the circuitry shown in FIG. 5.

Referring now to FIGS. 5 and 6, electrode elements 20 and 21 are shown extending through the molded plastic body 11 of the mouthpiece 10 and schematically illustrated as contacting the lips of the test subject. The electrical impedance of the lips is represented schematically by the resistor 55 at the surface of the lip 13 of the mouthpiece 10. At their other ends, electrode elements 20 and 21 have connected across them an impedance monitor circuit 57 and a signal generating circuit 59 which are preferably housed with and form a part of the circuitry of the breath tester or vehicle interlock (not otherwise shown) with which mouthpiece 10 is to be used. The circuitry for the interlock, including circuits 57 and 59 is preferably housed in a main control module (not shown) mounted under the dashboard of the vehicle. The mouthpiece 10 is removably connected to a sampling head 60 to form a part thereof. Sampling head 60 is in turn linked to the control module by way of a cable which includes conductors 67 and 68 which connect circuits 57 and 59 to electrode elements 20, 21 by way of a socket 69.

Impedance monitor circuit 57 provides means for helping to avoid evasion of the breath tester or vehicle interlock by attempting to filter a breath sample or couple a bogus gas delivery device such as a balloon or hose to mouthpiece 10. This is accomplished by sensing the resistance across electrode elements 20 and 21 during a test and generating a signal effective to abort the test sequence if the impedance across elements 20 and 21 is not within an expected range for contact with the mouth or lips of a person. It has been found that where electrode elements 20 and 21 are spaced about ⅛ of an inch apart at their exposed surfaces on the lip 13 of mouthpiece 10, the impedance monitor circuit 57 should be calibrated to accept the shunting of elements 20 and 21 by a resistance in the range of from about 20 kilohms to about 200 kilohms. This range is believed typical of the range expected for human lips moistened with saliva. In this way, the presence of a human user can be electrically distinguished from contact with a surface falling outside the expected resistance range such as the surface of a hose end or filter element. Further, the continuous presence o the proper impedance can be monitored by the interlock. An interruption or rapid change in the impedance during a test sequence as may be caused by a removal of the test subject's lip from across electrode elements 20, 21 can be used to detect a passing of the tester from one person to another and cause the test to be aborted.

In addition to the sensing functions just described, electrode elements 20 and 21 may also be employed, on a time-multiplexed basis if desired, to perform a signalling function. Under the control of the interlock C.P.U., a small A.C. signal can be gated to electrode elements 20 and 21 to cause a perceptible yet, not painful, stimulation of the test subject's lip or tongue. This signal may be used as a cue to the subject for various purposes such as indicating the proper time to commence an attempt to perform an identity-confirming act or start and/or cease delivery of a breath sample. As explained in the above referenced patent application, if critical events associated with the identity-confirming act are not performed in their proper time window, the test is aborted.

FIG. 6 shows a circuit for an impedance monitor 57 to ensure that the mouthpiece 10 is in contact with a person's lips and that contact is maintained substantially continuously, during the entire test. The circuit 57 measures impedance between the two electrode elements 20 and 21. Resistor 101 is about 200 kilohms and it is connected to the positive power supply terminal 115 whose voltage is about 1.0 volts. Lips moistened with saliva typically have a resistance in the range of about from 20 kilohms to about 200 kilohms. If wetted lips, represented by resistive element 55, bridge elements 20 and 21, there will be a current path from the positive power supply terminal 115, through resistor 101, through terminal 20, across the lips to the grounded contact element 21. If the impedance connected across terminals 20 and 21 is between about 20 kilohms and about 200 kilohms, the voltage between terminals 20 and 21 will be from about 0.09 v to about 0.5 volts. If a material with greater resistance, for instance cloth or rubber is in contact with the terminals, the voltage will be greater than about 5 volts. If the terminals 20 and 21 are connected with an electrical conductor or a material with resistance of less than 20 kilohms, the voltage will be less than about 0.09 volts. Diodes 102 and 103 protect the circuitry from static discharges as may be generated when clothing slides across upholstery. Electrode element 20 is connected to the positive input of an operational amplifier 104 which has its output connected to its negative input in the well known "voltage follower" connection to provide an extremely high input impedance and a unity voltage gain so that the electrode 20,21 is not loaded by the amplifier and the output voltage of the amplifier is very close to the input voltage. The output of the operational amplifier 104 is connected to the positive input of a comparator 108 and the negative input of a second comparator 112. Comparator 108 compares the output of the operational amplifier 104 to a voltage determined by the resistances of a voltage divider formed by resistor 105, potentiometer 106 and resistor 107. The resistor values and the setting of the potentiometer are such that the voltage at the negative input of comparator 108 is approximately 0.5 volts. If voltage of the positive input of the comparator 108 rises above a trigger voltage, which is about the voltage of the negative input, or about 0.5 volts, the output of the comparator 108 will rise. If the negative input voltage is less than the trigger voltage, the output voltage of the comparator 108 will remain low. Potentiometer 106 permits adjustment for tolerance in the trigger voltage of comparator 108 and component value tolerances in the rest of the circuit.

Similarly, if the voltage at the negative input of comparator 112 is below about 0.09 volts which corresponds to the threshold set by resistors 109, 111 and potentiometer 110, the output of comparator 112 will rise and if the voltage at the negative input of comparator 112 is greater than about 0.09 volts, the output will remain low. Potentiometer 110 permits adjustment of the trigger voltage of comparator 112 in a manner similar to the way potentiometer 107 operates with respect to comparator 108. If the inputs to comparators 108 and 112 remain between about 0.09 and about 0.5 volts, both comparators outputs will remain low. Since the input voltage to comparators 108 and 112 is the output of operational amplifier 104 and since the output of the operational amplifier 104 is very close to the voltage across terminals 20 and 21, the outputs of comparators 108 and 112 will both remain low if the resistance across terminals 20 and 21 is in the range of about 20 kilohms to about 200 kilohms.

A logic circuit consisting of NOR gate 113 and inverter 114 combines the outputs of comparators 108 and 112 such that the output 116 of inverter 114 remains in a low state if the impedance across electrode elements 20, 21 is in the 20 kilohms to 200 kilohm range. The signal appearing at the output 116 is connected to a data input port of the central processing unit (C.P.U.) (not shown) which controls the vehicle interlock. The software program stored in the C.P.U. causes it to poll line 116 at rapid rate during a test sequence including performance of the identity-confirming act, if one is required, and delivery of the breath sample. If line 116 goes high during such times, the C.P.U. causes the test to be failed.

Diodes 102 and 103 can be silicon signal diodes such as 1N914. Operational amplifier 104 can be of type LM301. Comparators 108 and 112 can be type LM 193. NOR gate 113 can be type 4001. Inverter 114 can be type 4069.

FIG. 6 also shows a signal generating circuit 59 for a vehicle interlock using mouthpiece 10. It has been found that a signal with an amplitude of about 5 volts peak to peak and a frequency of about 100 Hz produces a noticeable but not painful sensation on wetted lips. The circuit consists of an oscillator formed by logic inverters 201, 202 and 203 along with resistor 205 and capacitor 204. The inverters are connected to form a complete feedback loop which operates as follows: If the output of inverter 203 is high, this will cause the input to inverter 201, connected to the output of inverter 203, to be high, which causes the output of inverter 201 to be low. The output of inverter 201, connected through capacitor 204 holds the input of inverter 203 low which holds the output of inverter 203 high. Since the output of inverter 201, connected to the input of inverter 202, is low, this causes the output of inverter 202 to be high. This high voltage on the output of inverter 202 charges capacitor 204 through resistor 205. When the voltage at the input of inverter 203 rises due to the charging of capacitor 204 to a high enough level, the output of inverter 203 will go low. This will cause the output of inverter 201 to go high and the output of inverter 202 to go low. This will hold the input of inverter 203 high until capacitor 204 discharges through resistor 205, when output of inverter 203 will go high again. The cycles will endlessly repeat at a frequency, preferably about 100 Hz, determined principally by the values of resistor 205 and capacitor 204. The output voltage will be determined by the power supply voltage feeding the inverters. Resistor 206 is about 20 kilohms; it limits the current load on inverter 203 to prevent destroying the device if the output terminals 20 and 21 are shorted together. A D.C. blocking capacitor 210 insures that the signal appearing at electrode elements 20, 21 is a substantially pure A.C. signal. The three inverters 201, 202 and 203 can be three devices contained in a single type 4069 hex inverter, which contains six inverters.

As further illustrated in FIG. 6, circuits 57 and 59 are preferably selectively connected to electrode elements 20 and 21 in a time-multiplexed fashion under the control of a gate signal 211 generated under program control by the interlock C.P.U. Gate signal 211, when in a logical "high" state energizes a two pole, reed relay 212 to connect impedance monitor circuit 57 to contact element 20 via contact 213 to permit impedance sensing as previously described. At other times, when it is desired to output an electrical cue over elements 20, 21, reed relay 212 is deenergized by the interlock C.P.U. causing gate signal 211 to go to a logical "low" state. Reed relay 212 then connects contact element 20 with its contact 214 so that the signal generated by circuit 59 appears across electrode elements 20 and 21.

Figure 7:
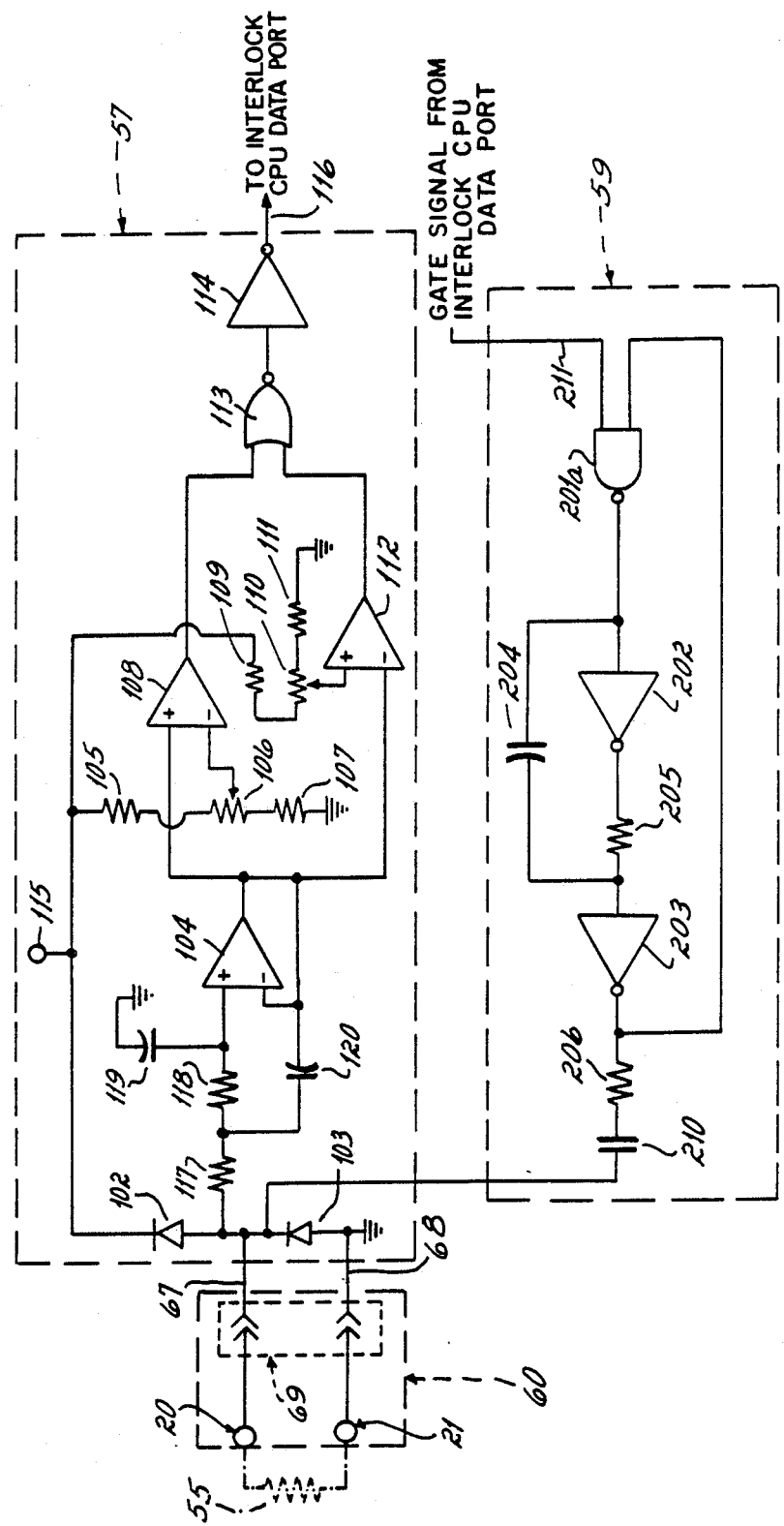
FIG. 7 is a schematic diagram illustrating an alternative to the circuitry of FIG. 6.

FIG. 7 illustrates an alternative way of connecting circuits 57 and 59 to electrode elements 20, 21 which does not require switching the connection of electrode elements 20, 21 between circuits 57 and 59. To avoid unnecessary repetition, it is to be assumed that except as pointed out below, the structure and operation of the circuitry of FIG. 7 is similar to that of FIG. 6 with like reference numerals designating like items.

In the circuitry of FIG. 7, relay 212 is eliminated and the output of signal generator circuit 59 is connected directly to the input of impedance monitor circuit 57 and also to electrode element 20 by way of line 67 so that the impedance 55 shunting electrode elements 20, 21 is superposed on the output of circuit 59. To selectively apply a cuing signal generated by a circuit 59 to electrodes 20, 21, circuit 59 has been modified slightly by replacing inverter 201 with a two input NAND gate 201a. One input to NAND gate 201a is connected to the output of inverter 203 to provide feedback as in FIG. 6 while the second input to NAND gate 201a is connected to the gate signal line 211 from the interlock CPU. Therefore, rather than being continuously free running as in FIG. 6, the signal generator circuit 59 of FIG. 7 is gated "on" and "off" by the interlock CPU according to the signal on gate line 211 under program control as explained above.

To prevent the cue signal, when present, from interfering with the operation of impedance monitor circuit 57, the front end of circuit 57 is provided with a filter effective to block the cuing signal. This is accomplished by adding resistors 117 and 118 in series with the positive input of operational amplifier 104. A capacitor 119 is connected between the positive input of operational amplifier 104 and ground. One terminal of another capacitor 120 is connected between the junction of resistors 117 and 118 and the other terminal of capacitor 120 is connected to the negative input of operational amplifier 104. With these modifications, the two resistors 117 and 118, the two capacitors 119 and 120 along with operational amplifier 104 form a well known low pass active filter circuit with a cut-off frequency of about 5 Hz. Below about 5 Hz, the filter acts like a voltage follower and the action is as previously described. Above 5 Hz, the filter attenuates the signal increasingly with increasing frequency. The dc voltage indicating the impedance across terminals 20 and 21 is passed while the ac voltage due to the signalling across the same terminals is blocked.

Time multiplexing in the manner described above with reference to FIG. 6 or superposition of the sensing and signalling functions as just described with reference to FIG. 7 allow use of a single set of electrode elements 20, 21 for both sensing and signalling. Of course if desired, a second set of electrode elements (not shown) could be provided with circuits 57 and 59 wired separately to its own one of the two sets of electrode elements. The two sets of electrode elements could be implemented using three conductors, one of which would be common to both sets.

Cuing the test subject using direct electrical stimulation in the manner described above offers at least two important advantages over audible or visual signalling. First, if the subject does not have a sensitive area such as the lips or tongue in direct contact across elements 20 and 21 the cue will be missed and the test failed. This makes the successful manipulation of hoses, balloons, gas bottles and the like in attempt to circumvent the test very difficult. Further, if electrode elements 20 and 21 are shunted by either a conductive or insulative surface such as may be present on a filter element, the user will not be able to feel the cue signal and will fail the test. Note that this safeguard operates even if the surface of the filter happens to fall within the resistance range expected for human lips and therefore is not detectable by the impedance check described above.

While the above description constitutes a preferred embodiment of the invention and sets forth the best mode presently contemplated by the inventor of carrying out his invention, it is to be understood that the invention is not limited thereby and that in light of the present disclosure, various alternative embodiments will be apparent to those skilled in the art. For example, impedance monitor 57 could be modified to sense any combination of resistance, capacitance or inductance. Also, a single electrode could be provided on mouthpiece 10 with a second electrode provided elsewhere to contact another area of the test subject's body. Accordingly, it is to be understood that changes may be made without departing from the scope of the invention as particularly pointed out and distinctly claimed in the claims set forth below.

What is claimed is:

1. A breath test mouthpiece system, comprising:
   (a) a mouthpiece having an inlet for receiving a breath sample;
   (b) an electrode at least a portion of which communicates with the surface of said mouthpiece near enough to said inlet to contact the mouth of a user when receiving a breath sample from the user;
   (c) an impedance monitor circuit connected to said electrode for monitoring the impedance across said electrode; and
   (d) breath tester means connected to said mouthpiece for detecting a component in said breath sample.

2. The system of claim 1 further comprising:
   means connected to said impedance monitor effective to generate a signal upon the occurrence of at least one of, (a) contact of said electrode with means having an impedance lying outside a predetermined range during at least a portion of a predetermined interval and (b) an interruption in the impedance across said electrode during at least a portion of said predetermined interval.

3. A mouthpiece for delivering to a test apparatus a breath sample received through the mouthpiece from the mouth of a user, said mouthpiece comprising:
   a body having an exterior surface and a chamber within said body;
   said exterior surface having:
   (a) inlet means therethrough communicating with said chamber for receiving the breath sample from the mouth of a user,
   (b) outlet means therethrough communicating with said chamber for conducting a breath sample from said chamber to a test apparatus,
   (c) an outlet rim thereon surrounding said inlet means and facing approximately radially outward from said body,
   (d) delivery surface means thereon for substantially preventing encircling retention thereabout of supply means for delivering a bogus gas, which bogus gas supply means, if so retained in encircling relation thereabout, would deliver such gas through said mouthpiece to the test apparatus;
   said delivery surface means including:
   (e) mouth engaging surface means surrounding said inlet means, said mouth engaging surface means being substantially continuous and configured for making a sealing contact with the mouth of a user for thereby directing the breath sample from the user's mouth through said inlet means and into said chamber when the mouth of the user is pressed against said mouth engaging surface means,
   (f) a portion thereof radially outside of said mouth engaging surface means and radially inside of and bounded by said rim, said portion having at least one aperture means therethrough communicating with atmosphere at a location remote from said delivery surface means of said exterior surface for providing a gas leakage path from said delivery surface means for venting at least some of the bogus gas from said bogus gas supply means to atmosphere when said supply means is encircling and retained about the mouthpiece at said rim, said aperture means being so located between said mouth engaging surface means and said rim so that said gas leakage path does not vent to atmosphere a breath sample from the mouth of the user,
   (g) at least two electrodes at least a portion of each of which communicates with said mouth engaging surface means near enough to said inlet to contact the mouth of a user when receiving a breath sample from a user, said electrodes being capable of being connected in a circuit in the test apparatus, and
   (h) wherein said delivery surface means diverges at an angle of not less than about 30° from said inlet means to said rim, whereby said rim is the nearest portion on said exterior surface to said inlet means having a surface to which encircling self-retention of the bogus gas supply means can be made.

4. The mouthpiece of claim 3 wherein said inlet means includes an inner surface adjacent said mouth engaging surface means and which is tapered inwardly.

5. The mouthpiece of claim 3 further comprising:
   an electrode, at least a portion of which lies adjacent said mouth engaging surface means.

6. The mouthpiece of claim 5 wherein said portion of said electrode lies on the inlet side of said flange.

7. The mouthpiece of claim 3 wherein said body has a flange formed therein adjacent and radially outside of said mouth engaging surface means and having an outer edge defining said rim, said flange having an inlet side which is part of said delivery surface means and having a back side which is part of said exterior surface but which is not part of said inlet side surface means, said sides of said flange being separated from each other by said rim, and wherein said aperture is located in the inlet side of said flange and said leakage path extends between said sides of said flange from said aperture to said back side.

8. The mouthpiece of claim 7 wherein said aperture means includes an open side contiguous with the rims of said flange.

9. A breath test mouthpiece system, comprising:
(a) a mouthpiece having an inlet for receiving a breath sample;
(b) an electrode at least a portion of which communicates with the exterior surface of said mouthpiece near enough to said inlet to contact the mouth of a user when receiving a breath sample from the user;
(c) an impedance monitor;
(d) a signal generator; and
(e) breath tester means for detecting a component in said breath sample;
said impedance monitor and said signal generator each being connected to said electrode to permit monitoring of the impedance across said electrode and to permit energizing said electrode with a humanly perceivable signal adapted to cue a user of the mouthpiece by perceptible direct electrical stimulation.

10. A breath test mouthpiece system for cuing a user delivering a breath sample to be tested, said system comprising:
(a) mouthpiece means having surface means thereon with an inlet therethrough for receiving a breath sample from the user and an outlet capable of delivering said breath sample to an alcohol detector, said surface means being continuous and positioned for contacting the mouth of the user when receiving the sample from the user;
(b) at least two electrodes at least a portion of each of which communicates with said surface means of said mouthpiece means near enough to said inlet to contact the mouth of said user when receiving a breath sample form the user; and
(c) signal generator means connected to said electrodes for transmitting thereto a humanly perceivable electrical signal carrying information adapted to communicate with the user to cue the user of the mouthpiece means by perceivable direct stimulation of the mouth of the user when in contact with said electrodes.

11. The system of claim 10 wherein said signal comprises an A.C. signal.

12. A breath test system for testing a breath sample from the mouth of a user, said system comprising:
(1) a mouthpiece having a mouthpiece body, said body having an exterior surface surrounding said body and a chamber within said body, said exterior surface having an inlet therethrough communicating with said chamber fore receiving the breath sample from the mouth of the user and having an outlet therethrough communicating with said chamber;
(2) delivery surface means formed of said exterior surface and surrounding and adjacent to said inlet for allowing the formation of a substantially airtight seal between said inlet and the mouth of the user while substantially preventing the formation of an airtight connection by encircling self-retention thereabout of bogus gas supply means, said delivery surface means including:
(a) mouth engaging surface means formed of a first portion of said exterior surface, said first portion being:
(i) substantially continuous and surrounding said inlet for making a sealing contact with the mouth of the user for thereby directing the breath sample from the user's mouth through said inlet and into said chamber when the mouth of the user is pressed thereagainst, and
(ii) sloped outwardly from said inlet so as to diverge such that the encircling perimeter about said inlet increases with the distance thereon from said inlet at an angle sufficiently steep so as to inhibit such encircling self-retention thereabout; and
(b) venting surface means formed of a second portion of said exterior surface adjacent to and extending outwardly from said first portion on the opposite side thereof from said inlet, said second portion having aperture means therethrough communicating with atmosphere at a location remote from said delivery surface means for providing a gas leakage path from said portion for venting to atmosphere at least some of bogus gas from a bogus gas supply means if the supply means is encircling and retained about said delivery surface means, said aperture means being located so that said gas leakage path does not vent to atmosphere the breath sample from the mouth of the user seated against said mouth engaging surface means; and
(3) a breath tester connected to said outlet and having means therein for performing a test on the breath sample.

13. The system of claim 12 wherein said mouth engaging surface means adjoins said inlet and is inclined at an angle away from said inlet to deter mechanical connection of a bogus gas supply means thereto.

14. The system of claim 12 wherein said mouthpiece body has a flange formed therein adjacent to and radially outside of said mouth engaging surface means and having an outer edge defining a rim, said rim having an inlet facing side which is part of said delivery surface means and having a back side opposite said rim from said inlet facing side, and wherein said aperture means is located in said inlet side of said flange, and said leakage path extends between the sides of said flange.

15. A breath test system for communicating a cuing signal to a user of the system, said system comprising:
(a) a breath tester;
(b) a mouthpiece having inlet means for receiving a breath sample from the mouth of a user, said inlet means having mouth engaging surface means surrounding said inlet means, said surface being adapted for contacting the lip of the user when the breath sample is being received at said inlet means from the user's mouth;
(c) means interconnecting said mouthpiece and said tester for delivering the sample received at said inlet means to said tester;
(d) a signal generator for generating a humanly sensible cue signal; and
(e) means mounted in said mouthpiece for communicating said humanly sensible cue signal from said signal generator to the lip of the user when the user's lip is in contact with said surface means when the user's mouth is positioned to deliver a sample to said mouthpiece.

16. The breath test system of claim 15 wherein said signal is an electrical signal.

17. The breath test system of claim 16 wherein said signal communicating means communicates said signal through electrical contact with the lip of the user.

* * * * *